United States Patent [19]

Cipollini

[11] Patent Number: 4,654,075
[45] Date of Patent: Mar. 31, 1987

[54] EMULSION-CHAR METHOD FOR MAKING FINE POWDER

[75] Inventor: Ned E. Cipollini, Succasunna, N.J.

[73] Assignee: Sprague Electric Company, North Adams, Mass.

[21] Appl. No.: 745,045

[22] Filed: Jun. 17, 1985

[51] Int. Cl.$^4$ ............................................. C01B 31/00
[52] U.S. Cl. .................................. 75/0.5 A; 264/29.1; 264/29.6; 423/592; 423/593; 423/598
[58] Field of Search .................. 264/9, 15, 29.1, 4, 264/29.6, 29.7, 340, 56, 63; 423/593, 598, 592; 501/137, 135, 103, 108; 75/0.5 A

[56] References Cited

U.S. PATENT DOCUMENTS

| | | | |
|---|---|---|---|
| 3,250,832 | 5/1966 | Metz | 264/29.1 |
| 3,330,697 | 8/1963 | Pechini | 117/215 |
| 3,647,364 | 3/1972 | Mazdiyasni et al. | 23/51 R |
| 4,081,857 | 3/1978 | Hanold, III | 361/321 |
| 4,293,514 | 10/1981 | Wada | 264/61 |

FOREIGN PATENT DOCUMENTS 2032233 1/1971 Fed. Rep. of Germany .

Primary Examiner—Jan Silbaugh
Assistant Examiner—Mary Lynn Fertig

[57] ABSTRACT

Water soluble precursors of ceramic compounds are emulsified in an organic fluid that is subsequently heated to remove the free water from the emulsion droplets and further heated in a partial oxygen atmosphere to form a char. The carbon in the char maintains the separation between the dried droplet-derived particles. This char may then be heated in air to oxidize and remove the carbon, to calcine the ceramic, and to controllably produce a fine powder of spherical particles having a narrow size distribution.

20 Claims, 6 Drawing Figures

DRIED EMULSION

CHAR

CALCINED POWDER

EMULSION-CHAR METHOD FOR MAKING FINE POWDER

BACKGROUND OF THE INVENTION

This invention relates to a process in which a powder is produced by forming an aqueous solution including precursors of the powder material, mixing to emulsify the aqueous solution in a water-immiscible fluid, and drying and separating the emulsion droplets.

Ceramic materials are made by the thermal decomposition of metal organic resins. Such a method is described by M. Pechini in his U.S. Pat. No. 3,330,697 issued July 11, 1957, and assigned to the same assignee as is the present invention. This method provides highly homogeneous bulk material but not powder.

Finely divided ceramic materials have been made by emulsifying an aqueous solution of a metal salt in a water-immiscible liquid. The water of the emulsion is then evaporated without boiling away a significant part of the water-immiscible fluid, and the emulsion is transformed into a metal-salt sol. Subsequently, the sol is caused to coagulate (flocculate) e.g., by heating and/or by the addition of a propanol, ethanol, or the like. The heating is also for simultaneously thermally decomposing the metal salt to produce a refractory powder.

Another method, dedicated to making alkali-earth-metal titanate powders, begins by forming alcoholates of each of the precursor metals, mixing the alcoholates and refluxing the mixture, adding water to the mixture to form a precipitate, separating the precipitate from the solution and drying the recovered titanate powder.

The later two processes, by which particles of metal compounds are separated by precipitation from a solution, are capable of producing fine powders, but inevitably some of the fine particles so produced agglomerate to form large particles.

It is therefore an object of this invention to provide a method for making a finely divided powder of a wide range of compositions.

It is a further object of this invention to provide such a method wherein initially the powder product precursors are dissolved in an aqueous solution that is emulsified to establish the ultimate sizes of the final powder particles.

It is yet a further object of this invention to provide such a method wherein the emulsion is subjected to drying to form a dispersion and heating the dispersion in an essentially inert atmosphere to char the dispersion whereby the carbon in the char maintains separation of the dried particles.

SUMMARY OF THE INVENTION

A method for making a fine powder comprises preparing an aqueous solution of precursor compounds of the desired powder product and forming an emulsion of the aqueous solution in a water-immiscible organic fluid. The emulsion is heated to remove the water from the droplets, thus converting the emulsion to a dispersion of particles that are composed of the precursor compounds. Heating is continued to evaporate and remove a substantial portion of the organic fluid. A subsequent heating is performed in an essentially inert atmosphere to decompose the remaining portion of the organic fluid to form a carbon char and a char matrix in which separation of the particles is preserved. Finally, oxidation of the carbon in the char is effected by heating in a controlled oxygen atmosphere to remove the carbon, leaving only the particles in the form of a powder.

The process of this invention is capable of producing fine powders of great compositional variety. It is particularly well suited for making metal oxides, glasses, and ceramics for which water-soluble precursors are widely available. It is foreseen that pure metal powders can be made by this process, particularly silver, palladium, platinum and gold that would be useful for making very thin precious metal electrodes in electronic components.

Success in making fine powder particles according to this invention is dependent upon taking particular measures during the removal of water and the subsequent oxidation following charring of the organics to insure that neither the emulsion droplets nor the particles in the later steps combine. The finer the particles become, the more difficult this is to achieve because smaller particles have higher surface energy and a greater tendency to agglomerate.

The tendency for the emulsion droplets to flocculate and/or sediment is reduced by heating and removing the water slowly. The tendency for the particles to agglomerate in the late stages of the exothermic oxidation step is reduced by maintaining the temperature of the particles at a temperature less than the characteristic minimum reaction or calcining temperature of the precursor compounds of which the particles are composed. Such temperature control may be accomplished by controlling the amount of oxygen in the atmosphere, by heating only small thin sections of the char, and/or slowing the rate of heating.

The invention relies centrally upon the emulsion char step wherein separation of the dried particles of the ceramic precursors is preserved during heating in a partial-oxygen atmosphere by the residue of carbon generated during this heating. The fine powder product is consequently made up of particles each of which derives directly from a droplet in the mother emulsion.

The aqueous droplets in the emulsion contain precursor compounds in the ratios needed to produce the desired composition of the powder product. Thus, it is possible by the process of this invention to achieve precise control of the final powder composition, an advantage particularly important for making ceramic powders that are suitable for electronic applications. Furthermore, little if any comminution steps are required which tend to introduce impurities in ceramic compositions made by conventional powder grinding, mixing, calcining and subsequent grinding steps. In addition, the precursors are dissolved and very intimately mixed in the aqueous solution. Thus, not only is control of chemical composition (e.g., ceramic stoichiometry) more exactly effected but the method of this invention is capable of providing a purer product of unsurpassed compositional homogeneity.

This powder may be very fine and have a narrow particle size distribution. Both average particle size and size distribution strongly depend respectively upon the nominal size and size distribution of the droplets in the emulsion. And, the powder particles made by this process are inherently spherical. Spherical particles having a narrow size distribution are considered to be ideal for obtaining high packing densities as are desired for making dense ceramic and metal films in the electronics industry.

This invention thus provides a unique method whereby water soluble precursors of ceramic compounds may be emulsified in an organic fluid that is subsequently heated to remove water from the emulsion droplets and further heated in an essentially inert atmosphere to form a char and comprised of the decomposed organic fluid. The carbon in the char maintains the separation between the dried droplet-derived particles. This char may then be heated in air or in a controlled oxygen atmosphere to oxidize and remove the carbon, to subsequently calcine the ceramic, and in general to controllably produce a fine powder.

DESCRIPTION OF THE PREFERRED EMBODIMENTS

Preparation of a titanium citrate

Figure 1:
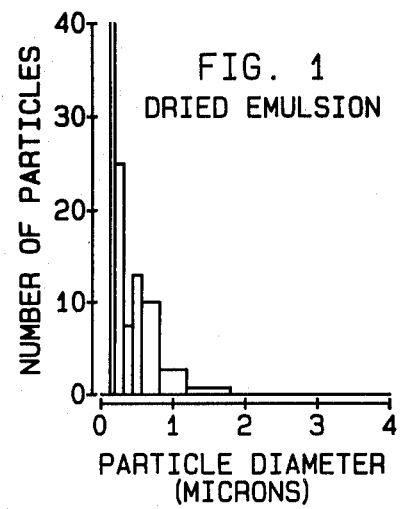
FIG. 1 shows a particle-size-histogram of particles at the dried-emulsion stage in a process of this invention for making barium titanate powder.

A 1500 milliliter (ml) quantity of double deionized water is dispensed into a 4 liter beaker. Into this beaker is stirred 1320 grams (gm) of anhydrous citric acid. The pH is brought to 4.0 by the addition of $NH_4OH$ (about 750 ml). To this is added 1500 ml of tetra-isopropyl titanate (TPT) at a rate of approximately 100 ml per minute. As TPT is added a white precipitate is formed that gradually disappears with stirring. The solution is then slowly heated to a temperature slightly above the boiling point of isopropanol, namely; 82.4° C., and maintained there while stirring for about 6 hours in order to remove the isopropanol. It is then cooled to room temperature and the pH is adjusted to about 5.0. This solution is diluted to 3000 ml by the addition of more double deionized water, and filtered through a medium grade filter paper to remove any undissolved solid particles. The resulting solution is titanium citrate 1.30 solution, by which it is meant that the molar ratio of citrate to titanium is 1.30.

At this point, the solution may be assayed for $TiO_2$ content, e.g., by ignition at 900° C. for 2 hours. It will be close to 11.00% $TiO_2$ by weight and will be assumed to have this level of titania in the following examples illustrating the use of this solution.

Preparation of a barium titanium citrate

Into another beaker there is weighed out 3117.4 gm of the titanium citrate 1.30 solution. To this is added 1500 ml double deionized water. While stirring, 756.46 gm anhydrous citric acid is added and dissolved in the solution. The solution is heated to 40° C. and 847.08 gm $BaCO_3$ is slowly added. The barium carbonate reacts with the citrate solution to form a clear fluid. It is then cooled to room temperature, the pH is adjusted to 5.4 using $NH_4OH$ and the solution is diluted until a density of 1.22 $gm/cm^3$ is obtained. This resulting solution is barium titanium citrate 2.22. This term is meant to indicate that the molar ratio of citrate to barium titanate is 2.22. Water is added to the solution to obtain a concentration of 0.1 mole barium-titanium citrate per 175 ml of solution. The volume produced amounts to about 7510 ml.

Preparation of an oil phase

Almost fifteen liters (14897 ml) of a high purity hydrocarbon solvent was poured into a large container. One such hydrocarbon is an isoparaffin solvent sold as ISOPAR M, a tradename of EXXON Company, USA (a Division of EXXON Corporation, Houston, Tex.). This material has an initial boiling temperature of 207° C. and a final boiling temperature of 260° C.

To the hydrocarbon solvent is added 2629 ml of a high boiling point hydrocarbon, in this case a mineral oil designated DRAKEOL #35, a tradename of Penraco of Butler, Pa. It is a mixture of paraffin and naphthene and has an initial boiling point of 346° C.

A surfactant, or emulsion agent, in the amount of 350.52 grams is added to the contents of the container which is then thoroughly mixed. This amounts to 20 grams surfactant per liter of liquid (oil). The particular surfactant used here is designated OLOA 1200, a tradename of Oronite Additives Division of the Chevron Chemical Company, Los Angeles, Ca. It is a derivative of succinimide and polybutane.

Emulsification

Add 7510 ml of the barium titanium citrate solution to the quantity (about 17800 ml) of oil phase made as described above. This addition is made while mixing in a Gifford-Wood Hoxo-Mixer. The resulting mixture is subsequently passed through a Gaulin Homogenizer (Model 15M-8TA made by A. P. V. Gaulin, Everett, Mass.) at a pressure of 1000 pounds per square inch (psi). The more times the emulsion is passed through this high shear homogenizer, the smaller become the droplet sizes. In the present example, the mixture is passed through the homogenizing valve three times.

Heating to remove water

Heating is initially conducted under a mild vacuum, i.e., 16–20 inches (406 to 508 mmHg). The temperature of the emulsion rises to about 70° C. before distillation of water from the emulsion droplets of aqueous barium titanium citrate is effected through the oil and out of the container. Without the vacuum, water tends to condense on the walls of the container above the emulsion and to drip back into the emulsion which triggers sedimentation of the aqueous droplets. As the heating continues, a foam develops over the surface of the emulsion. By adjusting the vacuum, the thickness of the foam is kept at about 1 inch (2.5 cm). The water removal process is endothermic and stabilizes the temperature at from 70°–85° C. even though the heating continues. When much of the water in the droplets has been removed, the emulsion temperature begins to rise again. At a temperature of 90° C. the vacuum is discontinued and heating is continued in air at one atmosphere. The heating is continued until the emulsion temperature reaches 130° C. at which point substantially all of the water has evaporated but only a small amount of the mineral oil, if any, has been removed.

The rate of heating is then increased to rapidly raise the temperature to 200° C. The citrate just begins to break down and decompose at 180° C. The heating rate is then made slow enough (temperature changes at from 1° to 2° per minute) so that the suspended particles in the emulsion remain in equilibrium with their oil phase surroundings and do not flocculate and/or sediment. When the temperature has reached about 270° C. essentially all of the low boiling oil (ISOPAR-M) and all of the water have been removed. Heating must not exceed the boiling and/or decomposition temperature of the surfactant or else the surfactant function of keeping the particles apart will be lost. The particular OLOA surfactant used here characteristically decomposes at about 270° C. and higher.

The "emulsion" is now cooled to room temperature. The remaining material will be orange-brown to black depending on the amount of $HNO_3$ that may have been used for adjustment in pH of the citrate.

This material is an oily slurry and is comprised of separate particles, each of which derived from one of the aqueous emulsion droplets. These dehydrated particles consist essentially of barium titanium citrate. The particles are suspended in and separated by mineral oil and surfactant, the paraffinic hydrocarbon solvent having been driven off at the above-described heating. The paraffinic hydrocarbon, ISOPAR-M begins to boil at 207° C. and is essentially all gone at this point.

Charring

A beaker of the oily slurry, or suspension, is placed in a one cubic foot retort, that is mounted in an oven. The retort is sealed. Nitrogen ($N_2$) is passed through the retort at the rate of 2 standard cubic feet (57) per hour to prevent oxidation. The suspension is then heated to 300° C. in 15 minutes. It is further heated from 300° C. to 500° C. in 3 hours and held at 500° C. for half an hour. It is then cooled to room temperature in about 4 hours, still in the nitrogen atmosphere.

As a result of heating in this inert atmosphere to 500° C., all of the organic materials, the mineral oil and the surfactant, have been charred. During this step the carbon being formed advantageously functions to maintain the separation between the amorphous particles.

Oxidation and Calcination

A layer of the char matrix of about 6 mm thickness is spread out on a silica boat and heated in air to 700° C. for an hour. This results in a thinner layer, wherein the carbon is removed as CO and $CO_2$ by the time the char reaches 500° C. At 700° C. the constituents of the particles have reacted to form barium titanate. The layer of material is further heated to 920° C. for thirteen hours to complete the reaction, or calcination. The resulting material is found to be crystalline barium titanate as evidenced by X-ray diffraction analysis.

The resultant white powder particles are spherical with a narrow particle size distribution.

During that process for making barium titanate powder, samples of the "dried" emulsion particles in the char and the particles in the calcined powder were subjected to particle size measurements and in some cases also were subjected to analysis by scanning electron microscope.

Figure 2:
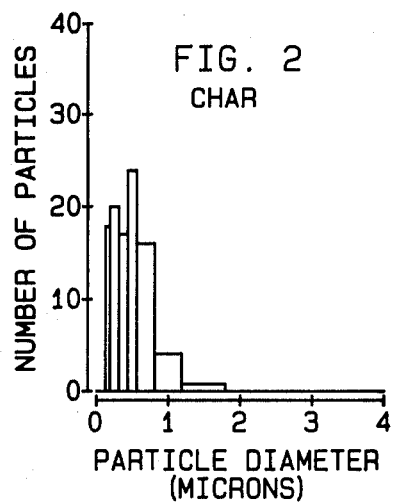
FIG. 2 shows a particle-size-histogram of particles at the char stage of the barium-titanate-making process, an earlier stage of which is characterized in FIG. 1.
Figure 3:
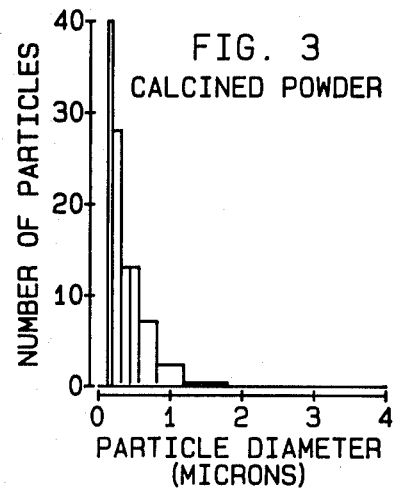
FIG. 3 shows a particle-size-histogram of barium titanate particles at the oxidized/calcined stage, earlier stages of which are characterized in FIGS. 1 and 2.
Figure 4:
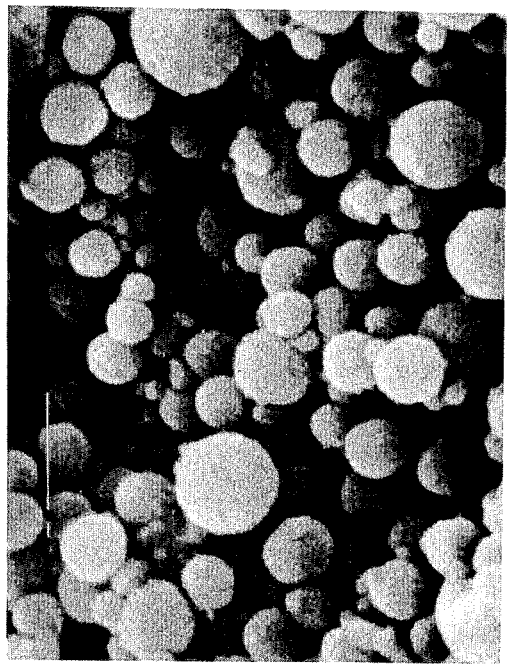
FIG. 4 shows a photograph of an S.E.M. image of powder particles characterized in FIG. 2.
Figure 5:
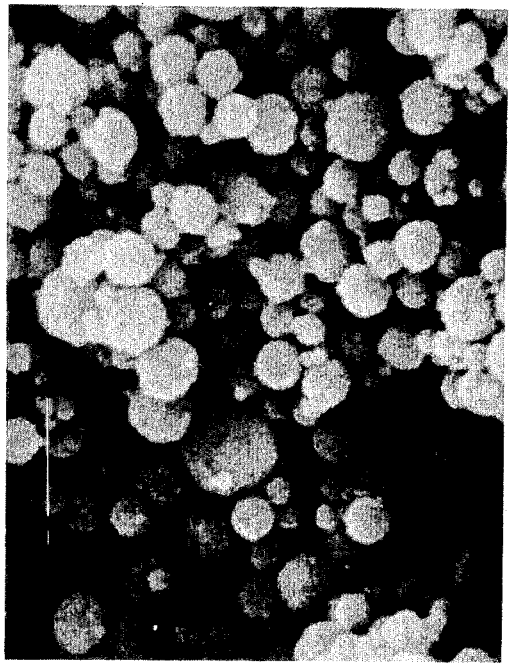
FIG. 5 shows a photograph of an S.E.M. image of powder particles characterized in FIG. 3.

Particle size measurments were made with a MICROTRAC (Trademark) Small Particle Analyzer (Model No. 7991-3) made by the Microtrac Division, Leeds and Northrup Co., Florida. This instrument uses light scattering to measure various parameters of particulate distributions. It employs laser illumination to a flowing stream of particles, producing diffraction patterns which are processed optically and electronically. This particular instrument does not see particles smaller than 0.12 micron. The number of particles in a sample having different ranges of diameters are shown in each of the bar graphs of FIGS. 1, 2 and 3, taken of the particle samples, respectively, from heated and "dried" emulsion, from the char, and from the oxidized/calcined final powder product. Electron-microscope photographs of particles from the char and from the final powder, respectively, are shown in FIGS. 4 and 5. The photographs were taken at a magnification of 20,000. The long bar in the photographs represents 1 micron.

There is apparently a slight increase in particle diameter going from the dried emulsion stage to the char stage, which increase could be due to the carbon coating on the particles. This theory is supported by the fact that the distribution for the calcined powder is very close to the distribution for the dried emulsion. The calcined powder is somewhat finer than the dried emulsion and char due to the expected shrinkage of particles that takes place during calcining. While there is a decrease in overall particle size on calcining, the distribution appears to be preserved. In fact, although the mean volume diameter changes slightly going from dried emulsion to calcined powder the distribution created by emulsifying is preserved in the final product.

Mechanisms and process limitations

In the above-described process, barium is introduced as barium carbonate, but other water soluble compounds of barium will also be effective such as the citrate, nitrate, and acetate salts of barium. Alkali and other alkaline-earth metals as well as many transition metals that are commonly found in glass and ceramic compositions form suitable water-soluble salts. Emulsions of this invention have actually been made employing the aqueous phase components, barium carbonate, barium acetate, barium nitrate, zirconium acetate and niobium oxylate. Other titanium salts than titanium citrate such as the tartrate, glycolate, acetate and lactate should be effective.

However, solubility in water is not enough. Each water-soluble precursor of the desired powder product must have a higher boiling point and decomposition temperature than the boiling point of water. This will make it possible to remove the water from the emulsion droplets by heating without removing the precursor.

The particular composition of the oil phase used in the fine-powder making process described above is but one of many that can be used effectively. The oil, or water-immiscible organic fluid, that is mixed with the aqueous salt solution and homogenized to form the emulsion, is preferably a mixture itself of a high boiling oil (e.g., the mineral oil) and a low boiling oil (e.g., the isoparaffinic solvent). As the temperature is gradually raised, the free water is first removed and then the lower boiling oil is driven off. The amount of the (remaining) high boiling oil determines the amount of carbon residue that forms at the subsequent char step.

It has been shown that the essential features of the process, i.e., its ability to control powder particle size, can be maintained even when the organic fluid is composed only of a high boiling oil (e.g., the above-noted mineral oil). However, the use of a single high boiling point oil requires more extensive heating and makes the emulsion formulation more critical.

This method permits a wide latitude in formulating the mixture that when homogenized becomes the emulsion. The formulation can thus be optimized for obtaining a desired droplet size and thus a desired powder particle size. After the emulsion has been formed an additional quantity of surfactant may be added if necessary. This additional surfactant does not affect droplet size but helps to stabilize the suspension during water removal. If too little surfactant is added to the emulsion, the droplets break and settle forming a sediment.

A substantial quantity of the surfactant is added to the oil prior to combining the oil with an aqueous solution of precursor salts. Droplet size diminishes as the quantity of this surfactant additive increases.

Surfactant quantities below 1 gram per liter makes formation of the emulsion difficult. In some cases, amounts beyond 40 grams per liter can prevent difficulties especially when ultra small powder particles are desired.

The temperature of the emulsion is gradually raised, preferably by supplying heat at a constant rate to the emulsion and preferably under a reduced pressure, e.g., about half of one standard atmosphere. At about 70° C. the water from the droplets begins to evaporate and the measured temperature of the emulsion remains at about 70° C. as more heat is applied until most of the water has been driven off. At this point the emulsion temperature rises and the emulsion of water and oil has been converted to a dispersion without the occurrence of coalescence.

It is concluded that a preferred oil phase composition includes a low and a high boiling point hydrocarbon. These two hydrocarbons must be mutually soluble and water immiscible. At least the high boiling hydrocarbon must leave a residue of carbon upon decomposing in a heated nonoxidizing (reducing) atmosphere and thus cannot "unzip" in a manner that fails to produce a carbon residue. The base hydrocarbons preferably include no metallic elements that may tend to react with and alter the material of the dried droplets. Thus, the residue resulting at charring from the hydrocarbons is preferably all carbon.

The process parameters of the charring step are not very critical. It is important, however, not to exceed the temperature at which the precursor compounds in the dried droplets will begin to interact because, in so doing, carbon may be incorporated into the reaction product. Such incorporation of carbon tends to modify the composition and degrade the properties of the final powder product, and detracts from an otherwise highly repeatable and controllable process.

Figure 6:
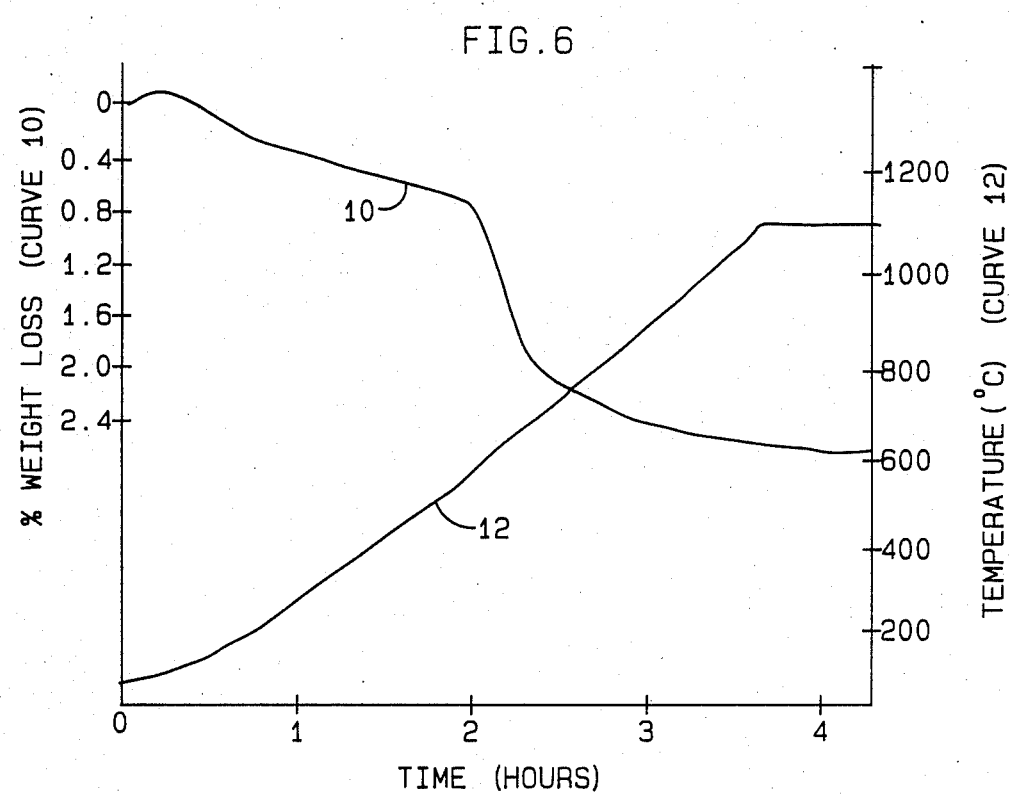
FIG. 6 shows a graph of oxidized powder of this invention being calcined plotting powder weight as a function of heating temperature.

In the process described above for making barium titanate powder, a sample of the char was heated and oxidized but at a temperature of only 500° C., and allowed to cool. This oxidized material, a white amorphous powder from which the carbon has been removed, was then heated to raise the temperature at a rate of 5° C./minute in air while measuring the weight of the powder. The change in powder weight as a function of time is plotted as curve 10 in FIG. 6 while the temperature is plotted as curve 12 as a function of time. It can be seen from these curves that the major reaction of calcining begins at about 550° C. During the major reaction or calcining from about 550° C. to 700° C. the weight loss amounts to 1.1% and the amorphous material of the particles reacts and is transformed to crystalline barium titanate as determined by X-ray diffraction analysis. Thus oxidation and removal of the carbon is essentially complete before the onset of calcination and crystallization.

The parameters in the oxidation step must be controlled. The main precaution necessary is to adjust the density or bulk of the char to be oxidized, and/or adjust the rate of heating or the amount of oxygen available in order to maintain control of the temperature at which this exothermic reaction takes place. If the reaction is uncontrolled the rise in temperature accelerates the reaction and an autocatalytic reaction will follow. If the exothermic reaction gets out of control, calcination could begin prior to complete oxidation leading to a carbon contamination of the product.

Preparation of Zirconium Acetate

Glacial acetic acid, 200 grams, is dispersed into a round bottomed flask and 100 grams of zirconium n-propoxide added. This mixture is stirred and refluxed for about 2 hours. A precipitate forms and may tend to stop the stirring action. Stirring should be maintained to prevent overheating.

The refluxed mixture is cooled and filtered through a medium porosity filter to remove the solids. The solids are vacuum dried at 60° C. for several hours producing about 65 grams of dried-solid zirconium acetate.

This material may be assayed for $ZrO_2$ by heating half an hour at 800° C. in air. It will indicate about 45% zirconia ($ZrO_2$) per gram of the dried zirconium acetate.

This zirconium acetate may be incorporated into the aqueous phase of an emulsion of this invention as a precursor of a powder product composed of a zirconium compound. For example, if it is the only precursor in the aqueous phase, the subsequent heating steps by which the emulsion is dried, charred and oxidized will produce a fine zirconia powder. Alternately, this zirconium acetate may be substituted for the titanium citrate in the above-described process for making barium titanate powder; the powder product thus produced is barium zirconate.

Preparation of a PLZT citrate

In a beaker, 29.69 grams $La(NO_3).6H_2O$ is dissolved in 160 ml double deionized water. In another beaker 110 grams anhydrous citric acid is dissolved in 100 ml water and the pH thereof is adjusted to 7.1 by the addition of $NH_4OH$. The lanthanum and citrate solutions are combined in a 1500 ml beaker to which 13.70/X grams of titanium citrate stock solution (described herein above) is also added. X is the weight fraction of $TiO_2$ in the stock solution as determined by assay. The pH is adjusted to 7.4 by adding $NH_4OH$. Also added is 112.23 grams PbO (litharge) which makes the mixture cloudy. The mixture is stirred and heated for about half an hour at 80° C. to render it clear. A further addition of 49.29/Y grams of zirconium acetate (for which the preparation is described above) is effected slowly while maintaining the pH at about 7 by introducing $NH_4OH$ as needed. Y is the weight fraction of zirconia in the acetate. Water may be added to adjust the volume to 1000 ml. The pH will be about 7.0 to 7.4.

Preparation of Magnesium Borate

An aqueous phase is made by dissolving 1.2 moles citric acid in double deionized water. Then 1.2 moles $MgCO_3$ is added to the solution and reacted with the citric acid solution to form a one M (molar) $MgHC_6H_5O_7$ solution. While continuing to heat and stir, 0.8 moles of $H_3BO_3$ is added at 40° C. until a clear green liquid is obtained.

This solution is emulsified in the immiscible hydrocarbon oil phase described above, except that 40 grams of the OLOA surfactant per liter of the oil was used. This mixture is emulsified in accordance with the above-described emulsification procedure, and heated to remove the water, also following the procedure described above in the process for making barium titanate powder. Charring is accomplished at 500° C. The char is oxidized at 715° C. for 1 hour and calcined at 920° C. for 16 hours in a standard air atmosphere. A fine $Mg_3B_2O_6$ powder is produced wherein 90% of the particles have a diameter less than 0.61 microns and the average particle size is 0.32. A few large particles in the 1 to 20 micron range appear to be agglomerates that formed in calcining. A slightly lower calcining temperature or a shorter calcining time or both are expected to eliminate such agglomerations.

What is claimed is:

1. A powder-making method of the kind including preparing an aqueous solution of precursor compounds of the desired powder product, and forming an emulsion comprised of a suspension of droplets of said aqueous solution in a water-immiscible organic fluid, wherein the improvement comprises:

heating said emulsion to evaporate and remove free water from said droplets and to evaporate and remove a substantial portion of said organic fluid to produce a dispersion of emulsion-droplet-derived particles in the remainder of said organic fluid;

heating said dispersion in a reduced-oxygen atmosphere to char said remainder of said organic fluid and to form a carbon-char matrix containing said particles; and oxidizing and removing the carbon in said carbon char matrix to leave only said particles in the form of a powder.

2. The method of claim 1 additionally comprising preparing said organic fluid by mixing together two organic liquids having a low and a high boiling temperature, respectively.

3. The method of claim 1 wherein said heating said emulsion includes raising the temperature of said emulsion no higher than the characteristic temperature at which said organic fluid begins to boil, until substantially all of said free water is removed.

4. The method of claim 1 wherein said heating said emulsion includes vacuum distillation to more effectively first remove said water and subsequently remove said substantial portion of said organic fluid.

5. The method of claim 1 wherein said heating said dispersion is accomplished by raising the temperature of said dispersion in an essentially inert atmosphere.

6. The method of claim 5 wherein said temperature is less than the characteristic temperature at which said precursor compounds react with each other.

7. The method of claim 1 wherein said oxidizing is accomplished by raising the temperature of said carbon-char matrix in an oxidizing atmosphere.

8. The method of claim 7 wherein said oxidizing temperature is maintained at less than the characteristic temperature at which said precursor compounds react with each other.

9. The method of claim 1 additionally comprising after said oxidizing, calcining said powder at a temperature greater than the temperature at said oxidizing.

10. A method for making a fine powder comprising:
    (a) preparing an aqueous solution of precursor compounds of the desired powder product;
    (b) forming an emulsion comprising a suspension of droplets of said aqueous solution in a water-immiscible organic fluid;
    (c) first heating said emulsion to remove free water from said emulsion droplets to convert said emulsion to a dispersion of dry particles composed of said precursor compounds;
    (d) heating said dispersion in an essentially inert atmosphere to decompose at least a portion of said organic fluid to form a carbon char matrix in which separation of said particles is preserved; and,
    (e) oxidizing and removing the carbon in said carbon-char matrix by heating in an oxidizing atmosphere to leave only said particles in the form of a powder.

11. The method of claim 10 wherein said precursor compounds each have a higher boiling point and a higher decomposition temperature than the boiling temperature of water so that said water is removed from said emulsion droplets during an early period of said first heating without removing said precursor compounds.

12. The method of claim 11 wherein said early period of said first heating is effected at emulsion temperatures that are less than the boiling point and the decomposition temperature of each of said precursor compounds.

13. The method of claim 11 wherein said water-immiscible organic fluid is comprised of at least one low boiling oil and at least one high boiling oil, and wherein said emulsion temperatures of said early period of said first heating are less than the initial boiling temperature of said organic fluid.

14. The method of claim 13 wherein after said early period, the emulsion temperature during the remaining period of said first heating is increased from said early period temperatures to a temperature intermediate the boiling temperatures of said at least one low and high boiling oils to remove said low boiling oil and retain said high boiling oil in said resulting dispersion.

15. The method of claim 14 wherein, at said further heating, said retained high boiling oil is said portion of said organic fluid decomposed to form the carbon char matrix.

16. The method of claim 10 wherein said organic fluid is comprised of a solution of a multiplicity of hydrocarbons at least two of which have different boiling temperatures.

17. The method of claim 16 wherein said hydrocarbons have compositions that are free of metals, to preclude the incorporation of said metals in the composition of said powder and to rely more exclusively upon the amounts and compositions of said precursor compounds for determining the composition of said powder.

18. The method of claim 17 wherein said organic fluid is additionally comprised of a hydrocarbon surfactant.

19. The method of claim 18 wherein said surfactant amounts to from 2 to 200 grams per liter of said organic fluid.

20. The method of claim 18 wherein during said first heating the temperature of said surfactant does not exceed the characteristic temperatures at which said surfactant decomposes and boils, respectively.

* * * * *